United States Patent
Lee et al.

(10) Patent No.: US 7,727,690 B2
(45) Date of Patent: Jun. 1, 2010

(54) IRIDIUM COMPLEX, CARBAZOLE DERIVATIVES AND COPOLYMER HAVING THE SAME

(75) Inventors: Jae-Suk Lee, Gwangju (KR); Nam-Goo Kang, Gwangju (KR); Hyo-Jin Jeon, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 147 days.

(21) Appl. No.: 11/941,599

(22) Filed: Nov. 16, 2007

(65) Prior Publication Data
US 2008/0177084 A1    Jul. 24, 2008

(30) Foreign Application Priority Data
Nov. 20, 2006    (KR) .................... 10-2006-0114467

(51) Int. Cl.
*C07D 401/10* (2006.01)
*C07D 401/12* (2006.01)
*C07D 209/82* (2006.01)

(52) U.S. Cl. .................. 430/58.6; 430/79; 546/276.7; 548/440

(58) Field of Classification Search .............. None
See application file for complete search history.

(56) References Cited

U.S. PATENT DOCUMENTS

2005/0147843 A1 *  7/2005  Kobayashi et al. .......... 428/690

FOREIGN PATENT DOCUMENTS

WO       WO 03/001616 A2    1/2003

OTHER PUBLICATIONS

You et al., "Blue Electrophosphorescence from Iridium Complex Covalently Bonded to the Poly (9-dodecyl-3-vinylcarbazole): Suppressed Phase Segregation and Enhanced Energy Transfer," *Macromolecules* 39:349-356 (2006).

* cited by examiner

*Primary Examiner*—Kamal A Saeed
*Assistant Examiner*—Michael Barker

(57) ABSTRACT

Disclosed are a monomer of iridium complex having a fluoro group as a functional group, a monomer of carbazole derivative having a hydroxy group as the functional group, and a copolymer containing the monomers in its main chain. The iridium complex used as a phosphorescent material and the carbazole derivative having an excellent hole transporting capability are synthesized as the monomer to form the copolymer. The content of iridium complex is easily controlled, and the carbazole derivative and iridium complex are contained in the main chain during the copolymer formation, thereby capable of manufacturing a light emitting device with higher heat resistance and chemical stability.

6 Claims, 8 Drawing Sheets

$^1$H NMR (300 MHz CDCl3) ä: 1.9(t) 2.5(d) 3.2(s) 3.8(t) 5.8(d) 6.8(m) 7.2(m) 7.5(m)

$^1$H NMR (300 MHz DMSO) ä: 0.8(d) 1.2(t) 4.5(t) 5.0(s) 6.9(t) 7.1(s) 7.2(d) 7.6(m) 8.2(d)

$^1$H NMR (300 MHz CDCl3) ä: 6.8(m) 7.2(t) 7.6(d) 8.0(m) 8.6(s)

$^1$H NMR (300 MHz CDCl3) ä: 7.0(t) 7.8(d) 7.9(d) 8.0(s) 8.4(s)

¹H NMR (300 MHz CD2Cl2) ä: 6.5(s), 6.8(t), 7.3(d)7.8(t)

¹H NMR (300 MHz CDCl3) ä: 6.6(m) 6.8(t) 6.9(t) 7.0(t) 7.2(d) 7.4(d) 7.5(m) 7.8(t)

$^1$H NMR (300 MHz CDCl3) ä: 0.8(t) 1.2(s) 1.6(t) 4.3(s) 6.8(d) 7.0(s) 7.2(s) 7.7(s) 7.9(t) 8.1(d) 8.8(s)

$^1$H NMR (300 MHz CDCl3) ä: 0.8(s) 1.2(s) 1.8(s) 2.0(m) 4.3(s) 6.8(d) 7.0(s) 7.2(s) 7.7(s) 7.9(t) 8.1(d) 8.8(s)

¹³C NMR (300 MHz CDCl3) ä: 14.08, 17.6, 22.6, 27.2, 29.5, 30.6, 31.8, 73.5, 77.02, 77.4, 109.05, 109.9, 118.67, 118.882, 119.54, 121.78, 123.4, 124.6, 125.1, 128.5, 128.6, 131.6, 132.5, 135.9, 137.8, 140.2, 149.5, 154.8, 155.59, 155.7, 158.9

$^{13}$C NMR (300 MHz CDCl3) ä:14.0, 17.6, 22.64, 27.2, 29.0, 29.24, 29.38, 29.58, 30.67, 31.8, 49.42, 109.0, 118.6, 118.87, 119.5, 121.78, 123.4, 124.6, 125.09, 128.5, 131.59, 131.53, 136.01, 140.2, 149.53, 154.81, 155.73, 158.9

IRIDIUM COMPLEX, CARBAZOLE DERIVATIVES AND COPOLYMER HAVING THE SAME

BACKGROUND OF THE INVENTION

1. Field of the Invention

The present invention relates to an organic light emitting material, more specifically, a copolymer having each monomer in its main chain, in which an iridium complex used as a phosphorescent material and a carbazole derivative having an excellent hole transporting capability are synthesized as the monomer.

2. Description of the Related Art

An organic light emitting device is a self-emissive display device that emits light by electrically exciting a fluorescent or phosphorescent organic compound. The organic light emitting device is advantageous in that it may be driven by a low voltage, manufactured in a thin film type, and has a wide viewing angle and fast response speed. Hence, the organic light emitting device can solve problems found in existing liquid crystal displays. Therefore, it has attracted attention as a next-generation display.

The organic light emitting device can be prepared by sequentially depositing a hole injecting layer, a hole transporting layer, a light emitting layer, an electron transporting layer, an electron injecting layer, and a cathode electrode on an anode electrode provided on a transparent substrate. All materials used in the organic light emitting device should have the preferred characteristics such that they have a high purity and are prepared by vacuum deposition. Further, the materials should exhibit high thermal stability at a glass transition temperature and thermal decomposition temperature, and be amorphous substances in order to prevent the deterioration of the device by crystallization due to Joule heat generated during device operation. The materials should also have good adhesion strength to other layers, but not move to other layers {Appl. Phys. Lett. 73, 1998, 729, Mat. science and Eng. R, 39, 2002, 143, Adva. Eng. Mat. Pro. Rep. 2002, 4, 453, Macromolecule 2003, 36, 9721, Adv. Mater. 2005, 17, 1109}.

Electrons in a compound may be in a singlet excitation state or a triplet excitation state. A probability of singlet state is a quarter, and the probability of triplet state is three quarters. Fluorescence occurs as the electron drops from the singlet state to the ground state, and phosphorescence occurs as the electron drops from the triplet state to the ground state. Therefore, the limit value of the internal quantum efficiency of light emitting material using fluorescence is 25%, and the limit value of the internal quantum efficiency of light emitting material using phosphorescence is 75%.

Further, the theoretical limit value of the internal quantum efficiency reaches to 100% in the energy transfer from the triplet excitation state to the singlet excitation state. The light emitting material, in which the luminous efficiency is improved by using such properties, is a phosphorescent material.

As the phosphorescent material, an organic metal compound is preferable, which has a transition metal with a high atomic number as a central atom undergoing intersystem crossing or energy transfer from the singlet or triplet excitation state to the triplet excitation state. It was found that as energy transfer is generated using an iridium compound as a sensitizer, the efficiency is rapidly increased {Inorg. chem. 1991. 30. 1685, NATURE 2000, 403 750-753, Appl. Phy. Lett. 77, 2000, 2280, Adv. Eng. Mat, 4, 2002, 453, J. Am. Chem. Soc. 2003, 125, 7379}.

In a single layer device having a structure of ITO(Indium-Tin-Oxide)/PVK(Poly-Vinylcarbazole)/Al, the maximum light emitting wavelength of purple color is 426 nm, and partially in the near UV region. A carbazole-based polymer is used to improve the luminous efficiency or color stabilization of organic light emitting device. In the case of using the system of blending other polymer with PVK (Polyvinylcabazole), the luminous efficiency is often rapidly increased, as compared to the case of using no PVK. In addition to a hole transporting characteristic, PVK forms a new light emitting species such as exciplex by interaction with a low molecular or high molecular weight material, thereby moving the light emitting wavelength {Syn. Mat. 1996. 80 271, Appl. Phys Lett 77, 2000, 2280, Adv. Mater. 2000, 12, 1949 Chem. Mater. 2004, 16, 442, Chem. Mater. 2004, 16, 4736}.

Many studies have been made on light emitting materials in the form of copolymer of the light emitting material and hole transporting material. It has been reported that the light emitting materials in the form of copolymer prevent phase separation and ionic aggregation, thereby capable of manufacturing a light emitting device, in which energy transfer to the light emitting material is efficient and stable, and its efficiency is excellent {Adv. Mater. 1999, 11, 285 J. Am. Chem. Soc. 2003, 125, 636, Organic Elctronics. 2003, 4, 105, Thin Solid Film. 2003, 353, 57, IEEE. 2004, 10, 115, Macromolecule 2006, 39, 349, J. Am. Chem. Soc. 2006, 128(20), 6647}.

SUMMARY OF THE INVENTION

In order to solve the above problems, it is an object of the present invention to provide a copolymer, in which an iridium complex or carbazole derivative is synthesized as a monomer, and the monomers are contained in the main chain by condensation polymerization.

DESCRIPTION OF THE PREFERRED EMBODIMENTS

Figure 1:
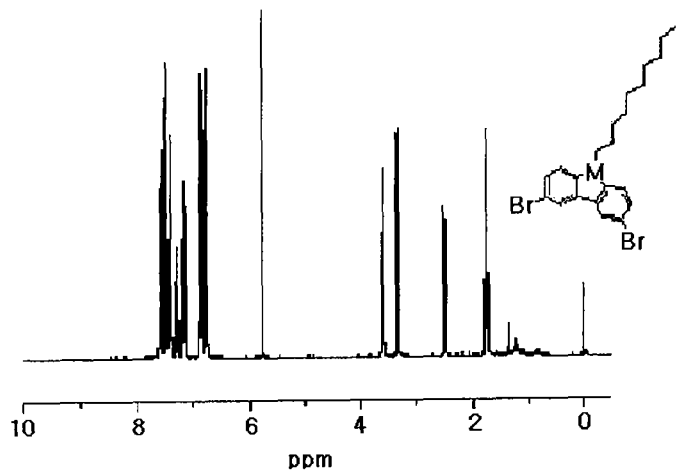
FIG. 1 illustrates the $^1$H-NMR spectrum of 3,6-dibromo decyl carbazole prepared in Preparative Example 1 according to the present invention.

In order to achieve the above object, the present invention provides a carbazole derivative and a preparation method thereof. Further, in order to achieve the above object, the present invention provides a monomer of iridium complex and a preparation method thereof. The carbazole derivative and iridium complex provided by the present invention are contained in the main chain of a copolymer by condensation polymerization.

Hereinafter, the preferred Example according to the present invention will be described in detail with reference to the accompanying drawings.

EXAMPLE

A monomer of carbazole derivative according to Example of the present invention is represented by the following Formula 1.

[Formula 1]

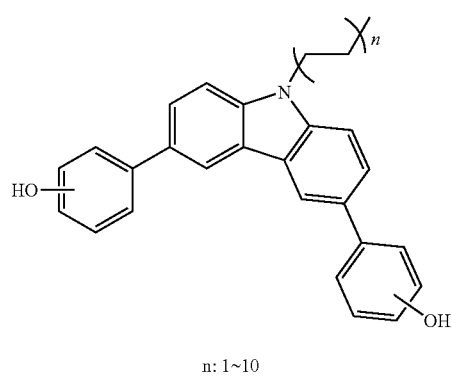

n: 1~10

The carbazole derivative disclosed in Formula 1 is synthesized according to the following Reaction Scheme 1.

[Reaction Scheme 1]

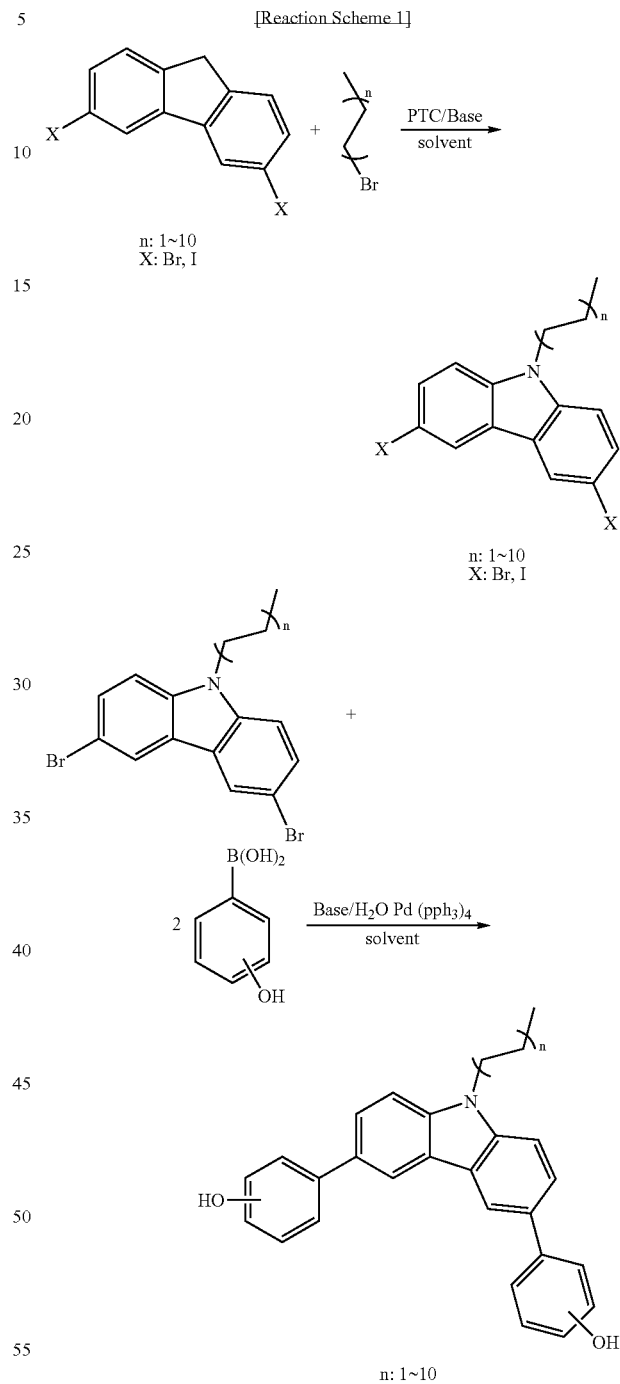

According to the first Reaction Scheme in Reaction Scheme 1, 3,6-dibromocarbazole was reacted in the presence of an alkali metal base catalyst and phase transfer catalyst, and bromoalkyl was linked to the 9-H position of carbazole to prepare a desired 3,6-dibromo-9-alkyl-carbazole. At this time, as the alkali metal base, sodium carbonate, potassium carbonate, sodium hydroxide, potassium hydroxide, or the like can be used, and as the phase transfer catalyst, a quaternary ammonium salt such as tetra-hexyl-ammonium-chloride, tetra-octyl-ammonium-bromide, crown ether, or the like can be used. As a reaction solvent, acetone was used. The reaction was performed at a reaction temperature of 70 to 80° C. for about 6 hours, and then terminated.

Using the 3,6-dibromo-9-alkyl-carbazole prepared as described above, 3,6-dibromo-9-alkyl-carbazole and hydroxy-phenyl-boronic acid were subjected to Suzuki coupling reaction in the presence of an alkali metal base and palladium catalyst as the second Reaction Scheme to prepare a desired dihydroxyphenyl-9-alkyl-carbazole. At this time, as the alkali metal base, sodium carbonate, potassium carbonate, sodium hydroxide, potassium hydroxide or the like can be used, and as the palladium catalyst, tetrakistriphenylphosphine, palladiumacetate or the like can be used. As the reaction solvent, tetrahydrofuran (THF), N, N-dimethylformamide (DMF), dimethylsulfoxide (DMSO), toluene, 1,4-dioxane or the like can be used. The Suzuki coupling reaction of Reaction Scheme 1 was performed in the temperature range of 80 to 120° C.

The monomer of iridium complex according to the present invention is represented by the following Formula 2.

[Formula 2]

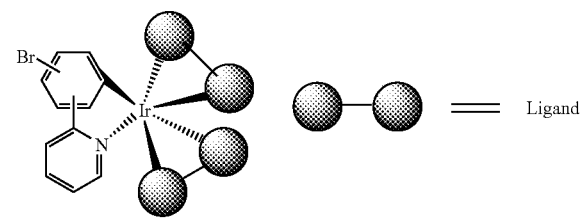

Ligand

| Name | Structure |
|---|---|
| 2-Phenyl-pyridine | 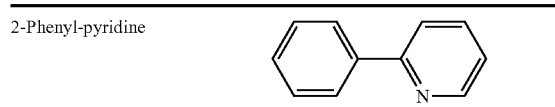 |
| 2-p-Tolyl-pyridine | 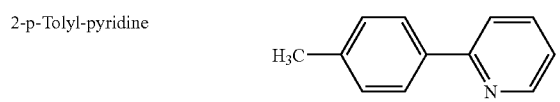 |
| 2-(4-Fluoro-phenyl)-pyridine | 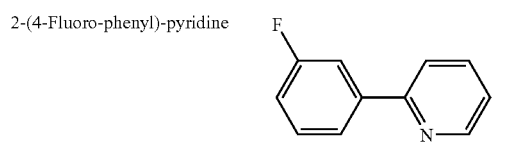 |
| 2-(2,4-Difluoro-phenyl)-pyridine | 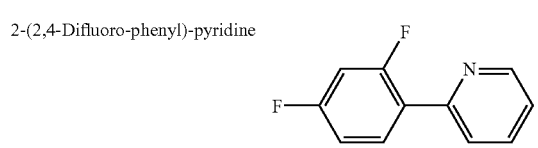 |
| Benzo[α]quinoline | 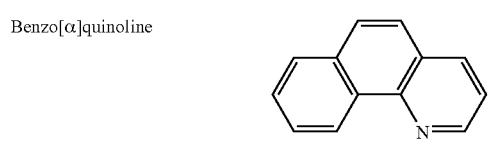 |

-continued

[Formula 2]

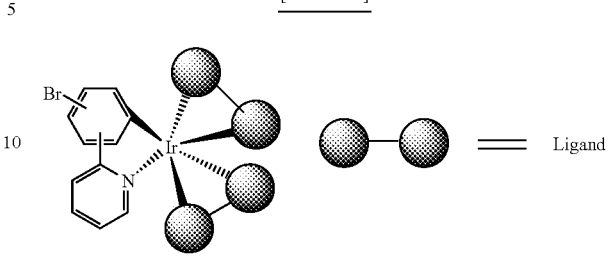

Ligand

| Name | Structure |
|---|---|
| 1-Phenylisoquinoline | 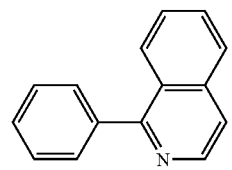 |
| 1-Naphthalen-2-yl-isoquinoline | 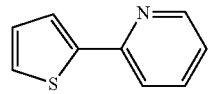 |
| 2-Thiophen-2-yl-pyridine | 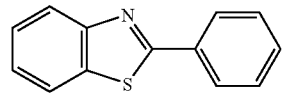 |
| 2-Phenyl-benzothiozole | 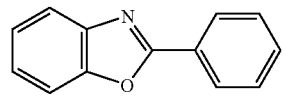 |
| 2-Phenyl-benzoenzooxezole | 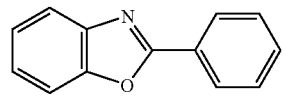 |
| 4-(5-ethylthio)-1H-tetrazol-1-yl)-2-fluorobenzonitrile | 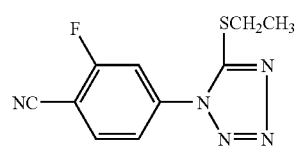 |
| 2-Biphenyl-4-yl-pyridine | 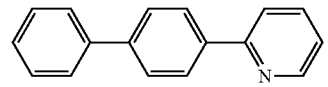 |

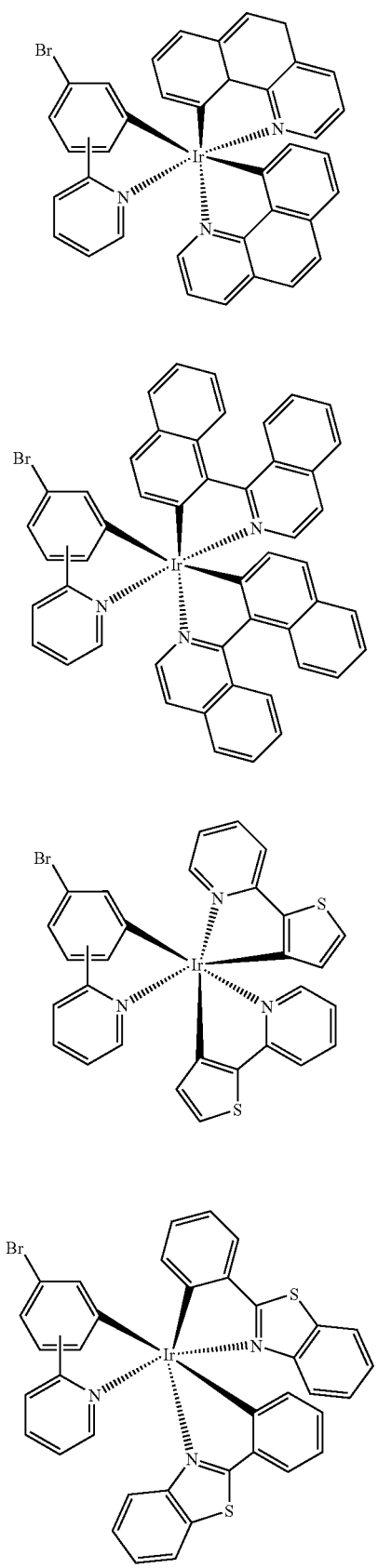
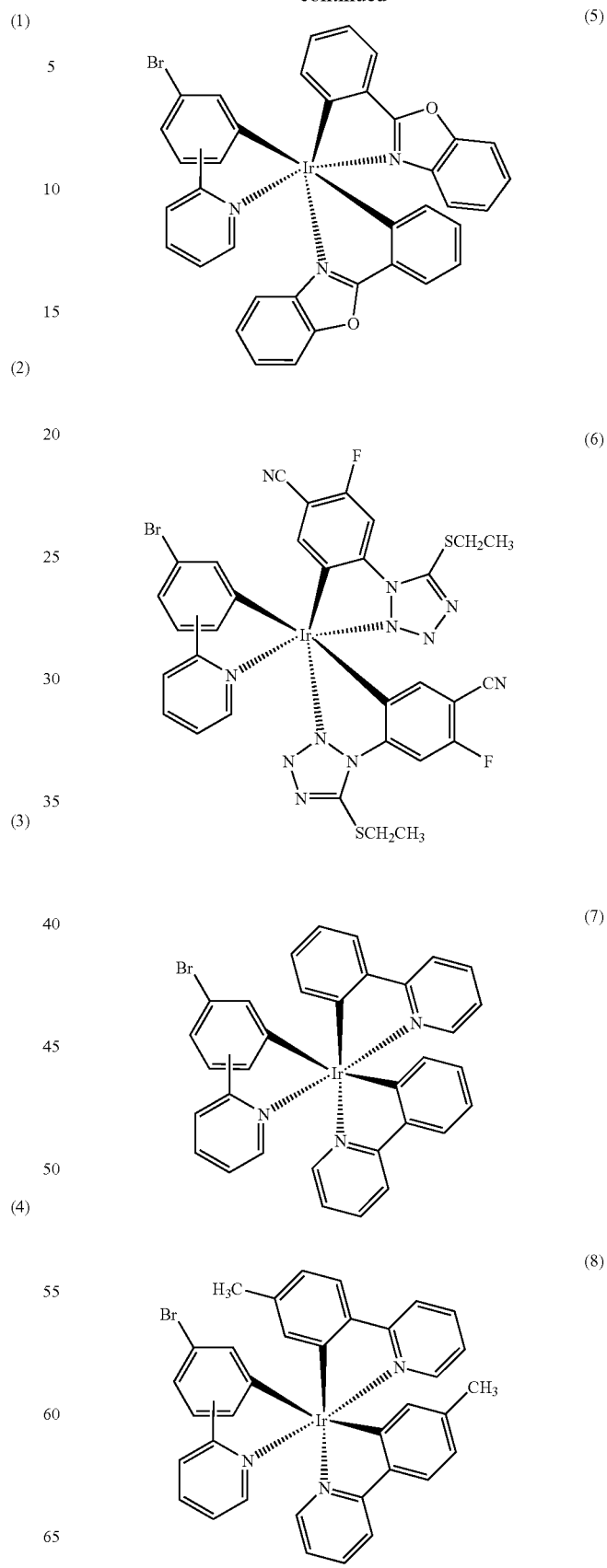

-continued

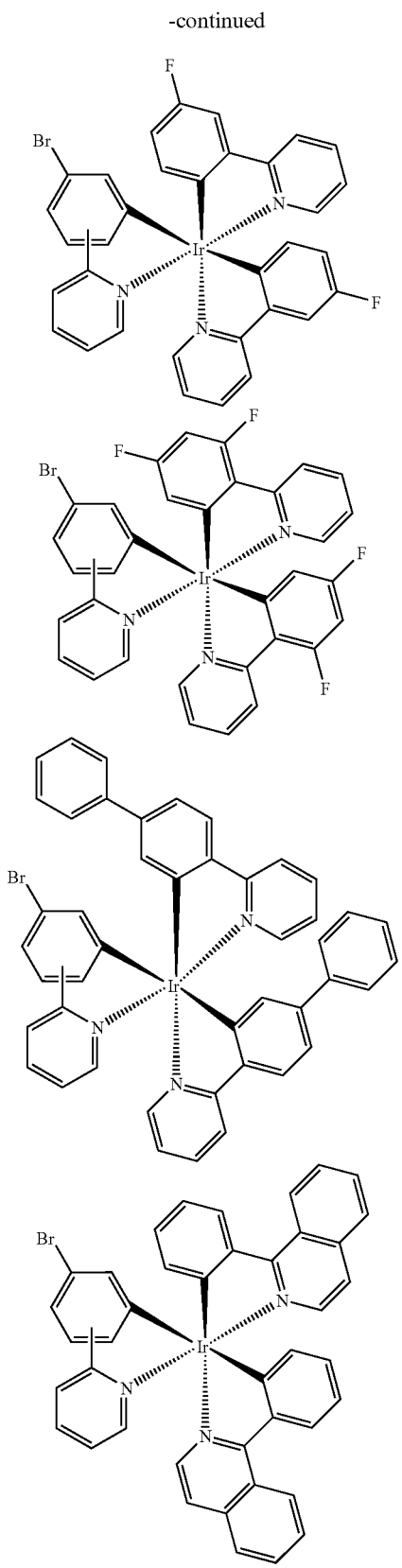

The monomer of iridium complex in Formula 2 can be synthesized as described in the following Reaction Scheme 2.

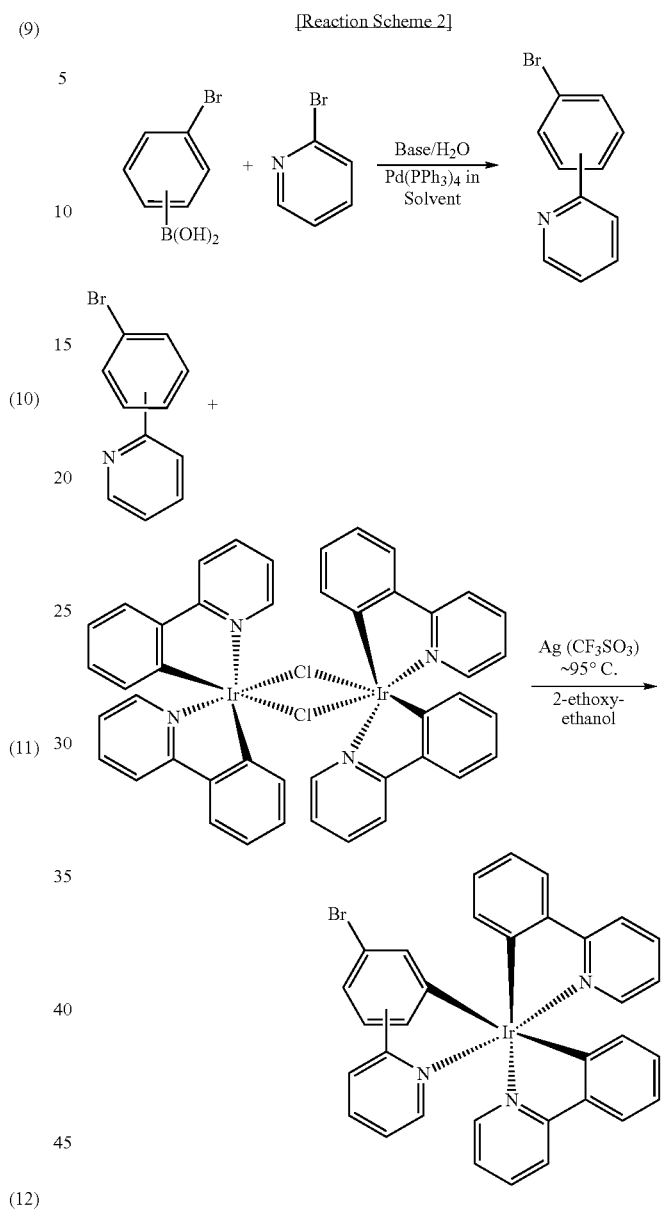

According to the reaction in Reaction Scheme 2, in the first step, bromopyridine was slowly added dropwise to bromo phenyl boronic acid in the presence of an alkali metal base and palladium catalyst, and subjected to Suzuki coupling reaction to prepare a desired bromo-phenyl-pyridine. At this time, as the alkali metal base, sodium carbonate, potassium carbonate, sodium hydroxide, potassium hydroxide or the like can be used, and as the palladium catalyst, tetrakistriphenylphosphine, palladiumacetate or the like can be used. As the reaction solvent, tetrahydrofuran (THF), N,N-dimethylformamide (DMF), dimethylsulfoxide (DMSO), toluene, 1,4-dioxane or the like can be used. The Suzuki coupling reaction of Reaction Scheme 2 was performed in the temperature range of 80 to 120° C.

Bromo phenyl pyridine and tetrakis(2-phenylpyridine-C, N)(μ-dichloro)diiridium prepared as described above were reacted in the presence of silver-tri-fluoro-methane-sulfonate catalyst to obtain a desired iridium(2-(4'-bromophenyl-4-yl) pyridine)(2-(2-(phenylpyridine))$_2$. As the reaction solvent, ethoxyethanol or the like was used, and the reaction was performed at a reaction temperature of 95° C.

Further, the monomer of iridium complex according to the present invention is represented by the following Formula 3.

[Formula 3]

| Name | Structure |
|---|---|
| 2-Phenyl-pyridine | 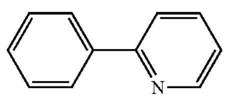 |
| 2-p-Tolyl-pyridine | 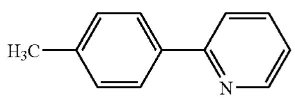 |
| 2-(4-Fluoro-phenyl)-pyridine | 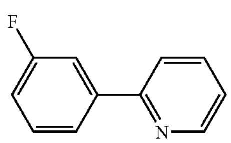 |
| 2-(2,4-Difluoro-phenyl)-pyridine | 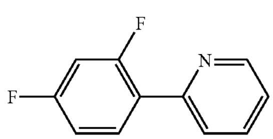 |
| Benzo[α]quinoline | 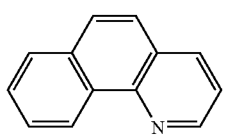 |
| 1-Phenylisoquinoline | 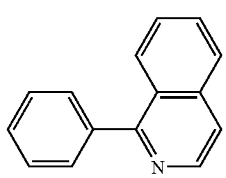 |
| 1-Naphthalen-2-yl-isoquinoline | 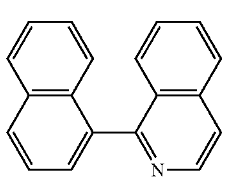 |
| 2-Thiophen-2-yl-pyridine | 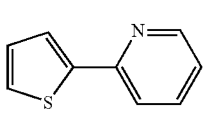 |

-continued

[Formula 3]

| Name | Structure |
|---|---|
| 2-Phenyl-benzothiozole | 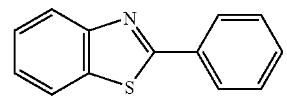 |
| 2-Phenyl-benzoenzooxezole | 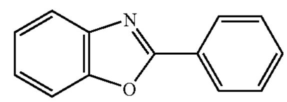 |
| 4-(5-ethylthio)-1H-tetrazol-1-yl)-2-fluorobenzonitrile | 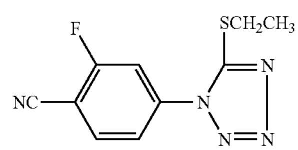 |
| 2-Biphenyl-4-yl-pyridine | 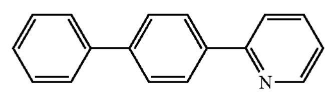 |

The monomer of iridium complex in Formula 3 can be synthesized as described in the following Reaction Scheme 3.

[Reaction Scheme 3]

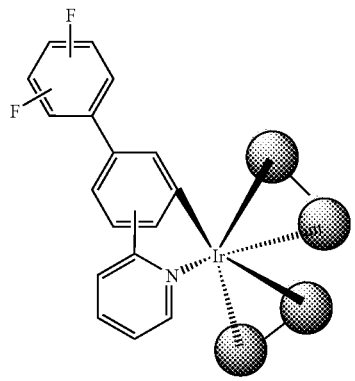

In Reaction Scheme 3, in the first step, bromopyridine was slowly added dropwise to difluoro phenyl boronic acid in the presence of an alkali metal base and palladium catalyst, and subjected to Suzuki coupling reaction to prepare a desired difluoro-phenyl-pyridine. At this time, as the alkali metal base, sodium carbonate, potassium carbonate, sodium hydroxide, potassium hydroxide or the like can be used, and as the palladium catalyst, tetrakistriphenylphosphine, palladiumacetate or the like can be used. As the reaction solvent, tetrahydrofuran (THF), N,N-dimethylformamide (DMF), dimethylsulfoxide (DMSO), toluene, 1,4-dioxane or the like can be used. The Suzuki coupling reaction of Reaction Scheme 3 was performed in the temperature range of 80 to 120° C.

In the second step, the prepared difluoro-phenyl-boronic acid and bromophenylpyridine-iridium complex were subjected to Suzuki coupling reaction in the presence of an alkali metal base and palladium catalyst to prepare a desired difluoro-phenyl-iridium complex.

At this time, as the alkali metal base, sodium carbonate, potassium carbonate, sodium hydroxide, potassium hydroxide, or the like can be used, and as the palladium catalyst, tetrakistriphenylphosphine, palladiumacetate or the like can be used. As the reaction solvent, tetrahydrofuran (THF), N,N-dimethylformamide (DMF), dimethylsulfoxide (DMSO), toluene, 1,4-dioxane or the like can be used. The Suzuki coupling reaction of Reaction Scheme 3 was performed in the temperature range of 80 to 120° C.

The synthesis of copolymer, in which the above described monomer were used and a molecular weight and iridium content were controlled, are illustrated in detail as follows.

[Formula 4]

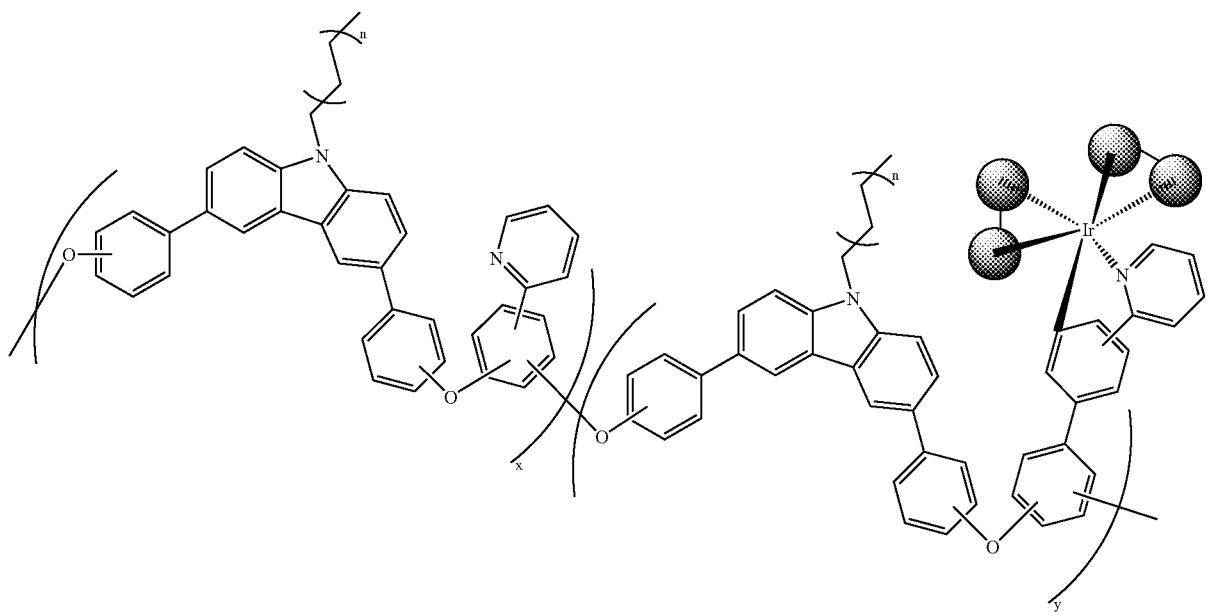

The copolymer in Formula 4 can be synthesized according to the following Reaction Scheme 4.
[Reaction Scheme 4]
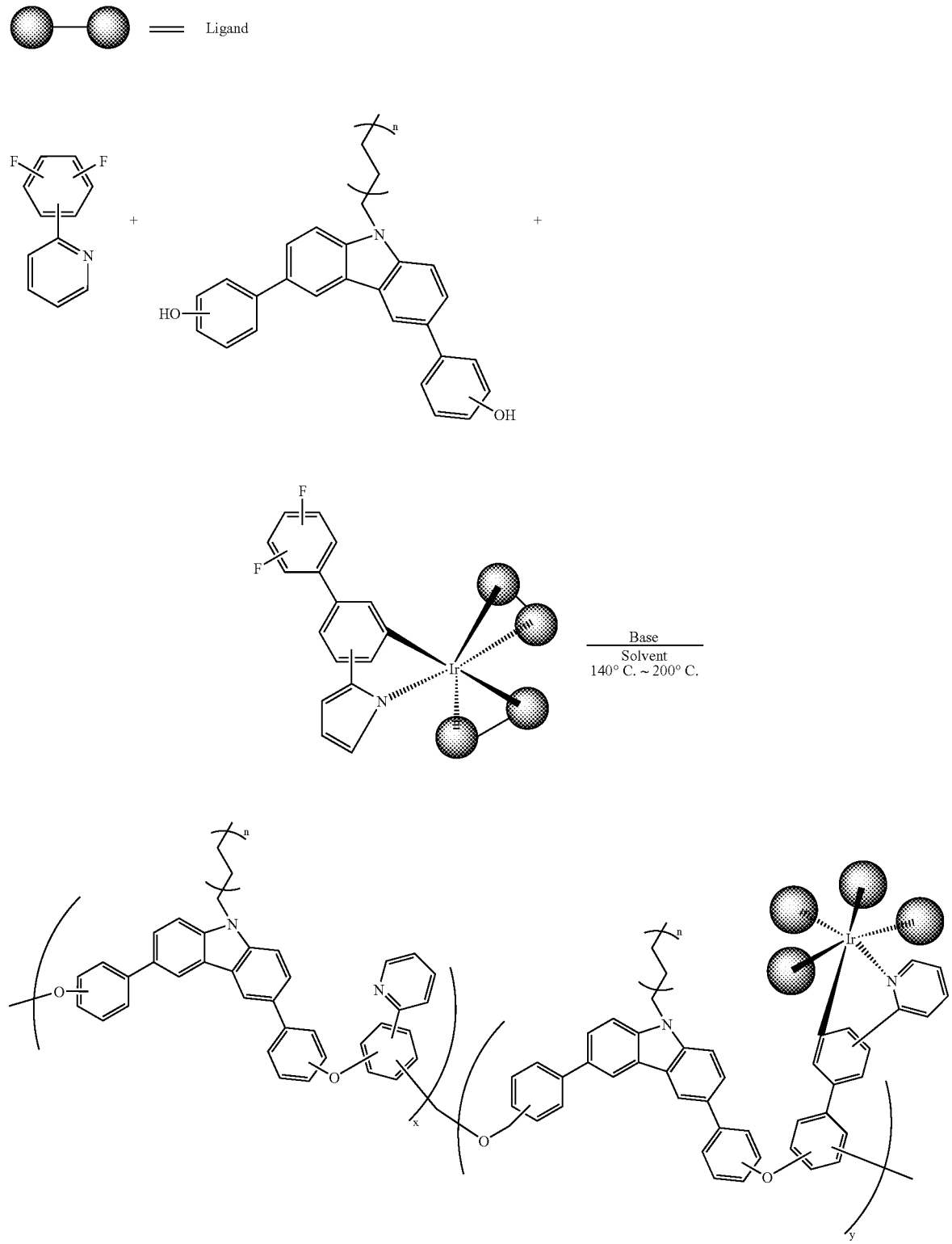

| Ligands | | | | |
|---|---|---|---|---|
| Structure | | | | |
| Name | 2-Phenyl-pyridine | 2-p-Tolyl-pyridine | 2-(d-Fluoro-phenyl)-pyridine | 2-(2,4-Difluoro-phenyl)-pyridine |
| Structure | | | | |
| Name | Benzo[χ]quinoline | 1-Phenyl-isoquinoline | 1-Naphtholen-2-yl-isoquinoline | 2-Thiophen-2-yl-pyridine |
| Structure | | | | |
| Name | 2-Phenyl-beniothiozole | 2-Phenyl-benzooxazole | 4-(5-(ethylthio)-1H-tetrazol-1-yl 2-fluorobenzonitrile | 2-Biphenyl-d-yl-pyridine |

According to Reaction Scheme 4, a dihydroxy phenyl carbazole derivative was activated in the presence of an alkali metal base. During activation, toluene or benzene was used as a co-solvent in order to remove water, and 1-methyl pyrrolidone, dimethyl-form-amide, dimethyl-sulfoxide or the like were used as a reaction solvent to be subjected to sputtering under nitrogen atmosphere for about 6 hours.

Then, a monomer with a difluoro group was added, and reacted for about 24 hours. In the first activation step, the reaction was performed at 150° C. The monomer with a difluoro group and difluoro-phenyl-iridium complex were added, and then reacted at 200° C. As the alkali metal base, potassium carbonate or the like was used.

As described above, the present invention will be illustrated in accordance with the following Examples. However, these Examples are for the illustrative purpose only, and the scope of the present invention is not intended to be limited by these Examples.

Preparative Example 1

Preparation of 3,6-dihydroxyphenyl -9-decyl-carbazole

First, in order to prepare 3,6-dibromo-9-decyl-carbazole, 0.3 g of tetra-octyl-ammonium-bromide (phase transfer catalyst) (0.00045 mol) was added to 5.0 g of 3,6-dibromo -9H-carbazole (0.015 mol), 4.0 g of 1-bromo decane (0.0165 mol), 2 g of sodium hydroxide (0.0225 mol), and 200 ml of acetone in a 250 ml double-necked, round-bottom flask under nitrogen atmosphere.

The mixture was refluxed at 80° C. for 6 hours, and the reaction was terminated. 500 ml of distilled water was put into a beaker, and the reaction mixture was poured therein, and extracted from 200 ml of dichloromethane three times. Then, 10 g of sodium sulfate was added, and stirred for 30 minutes using a rotary stirrer, and then the extracted mixture was filtered. The solvent was first removed using a rotary evaporator, and then the residue was purified by column chromatography using dichloromethane and hexane (1:1) as a developing solvent to be separated by rotary evaporation. The yield was 80%.

Further, an $^1$H-NMR of the prepared 3,6-dihydroxyphenyl-9-decyl-carbazole is illustrated in the accompanying FIG. 1. 5.5 g of 3,6-dibromo-9-decyl-9H-carbazole (0.012 mol), 5.0 g of 4-hydroxy phenyl boronic acid (0.036 mol), 150 ml of tetrahydrofuran and 2 M potassium carbonate aqueous solution (20 ml) were added to a 250 ml double-necked, round-bottom flask under nitrogen atmosphere, and palladium tetrakistriphenylphosphine (Pd(PPh$_3$)$_4$; 1.04 g, 3 mol %) as a catalyst was added thereto.

Figure 2:
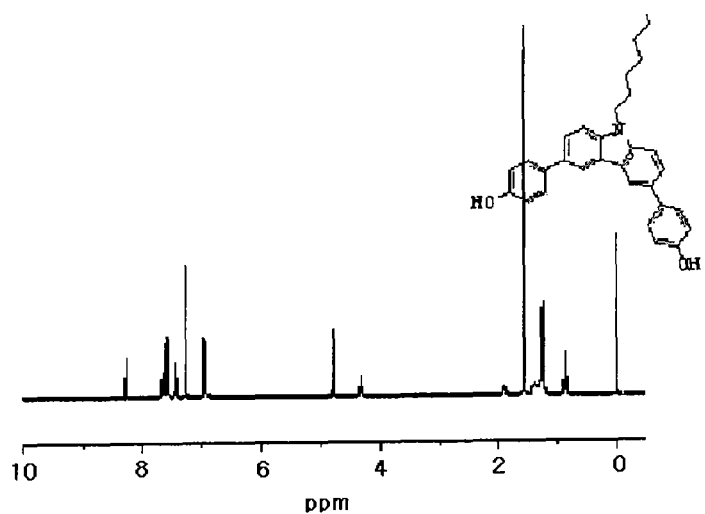
FIG. 2 illustrates the $^1$H-NMR spectrum of 3,6-dihydroxyphenyl-9-decyl-carbazole prepared in Preparative Example 1 according to the present invention.

The mixture was refluxed at 80° C. for 24 hours, and the reaction was terminated. 500 ml of distilled water was put into a beaker, and the reaction mixture was poured therein, and extracted from 200 ml of dichloromethane three times. Then, 10 g of sodium sulfate was added, and stirred for 30 minutes using a rotary stirrer, and then the extracted mixture was filtered. The solvent was first removed using a rotary evaporator, and then the residue was purified by column chromatography using dichloromethane and ether as a developing solvent to be separated by rotary evaporation. Finally, 3,6-dihydroxyphenyl-9-decyl-carbazole was prepared as in Formula 2, and the yield was 40%. Further, an $^1$H—NMR of the prepared 3,6-dihydroxyphenyl-9-decyl-carbazole is illustrated in the accompanying FIG. 2.

Preparative Example 2

Iridium(2-(4'-difluorophenyl-4-yl)pyridine)(2-(2-(phenylpyridine))$_2$

In order to prepare 2,4-difluoro phenyl pyridine, 5.0 g of 2,4-difluorophenyl boronic acid (0.0285 mol), 3.0 g of 2-bromopyridine (0.019 mol), 150 ml of tetrahydrofuran, and a 2M potassium carbonate aqueous solution (20 ml) were added in a 250 ml double-necked, round-bottom flask under nitrogen atmosphere, and then palladium tetrakistriphenylphosphine (Pd(PPh$_3$)$_4$; 0.7 g, 3 mol %) as a catalyst was added.

Figure 3:
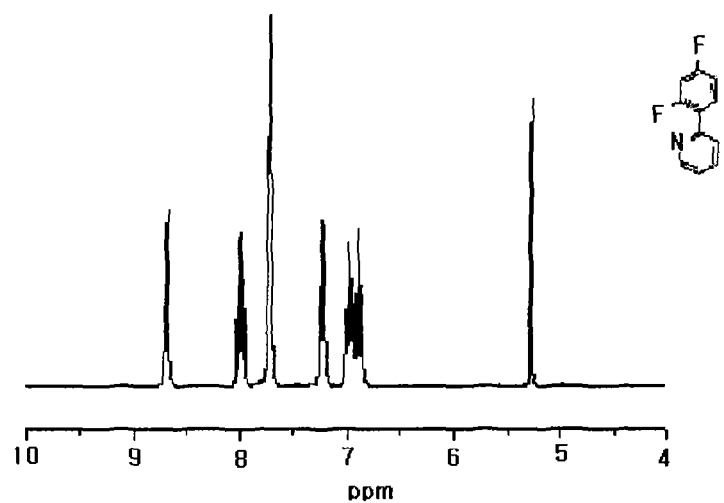
FIG. 3 illustrates the $^1$H-NMR spectrum of 2,4-difluoro phenyl pyridine prepared in Preparative Example 3according to the present invention.

The mixture was refluxed at 80° C. for 24 hours, and the reaction was terminated. 500 ml of distilled water was put into a beaker, and the reaction mixture was poured therein, and extracted from 150 ml of dichloromethane three times. Then, 10 g of sodium sulfate was added, and stirred for 30 minutes using a rotary stirrer, and then the extracted mixture was filtered. The solvent was first removed using a rotary evaporator, and then the residue was purified by column chromatography using dichloromethane as a developing solvent to be separated by distillation under reduced pressure. The yield was 83%. Further, an $^1$H-NMR of the prepared 2,4-difluoro phenyl pyridine is illustrated in the accompanying FIG. 3.

Figure 4:
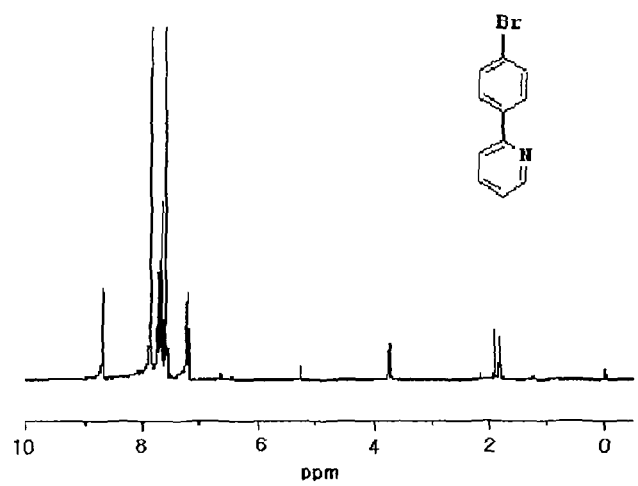
FIG. 4 illustrates the $^1$H-NMR spectrum of 4-bromo phenyl pyridine prepared in Preparative Example 2 according to the present invention.

Next, 1 g of bromo iridium complex (0.0014 mol), 0.5 g of 2,4-difluoro phenyl boronic acid (0.0021 mol), 150 ml of tetrahydrofuran, and 2M potassium carbonate aqueous solution (20 ml) were added in a 250 ml double-necked, round-bottom flask under nitrogen atmosphere, and palladium tetrakistriphenylphosphine (Pd(PPh$_3$)$_4$; 0.07 g, 3 mol %) as a catalyst was added. The mixture was refluxed at 80° C. for 24 hours, and the reaction was terminated 500 ml of distilled water was put into a beaker, and the reaction mixture was poured therein, and extracted from 200 ml of dichloromethane three times. Then, 10 g of sodium sulfate was added, and stirred for 30 minutes using a rotary stirrer, and then the extracted mixture was filtered. The solvent was first removed using a rotary evaporator, and then the residue was purified by column chromatography using dichloromethane as a developing solvent to be separated by rotary evaporation. Finally, iridium(2-(4'-difluorophenyl-4-yl)pyridine) (2-(2-(phenylpyridine))$_2$ was prepared as in Formula 3, and the yield was 86%. Further, an $^1$H-NMR of the prepared iridium(2-(4'-difluorophenyl-4-yl)pyridine)(2-(2-(phenylpyridine)) is illustrated in the accompanying FIG. 4.

Preparative Example 3

Iridium(2-(4'-bromophenyl-4-yl)pyridine)(2-(2-(phenylpyridine))$_2$

First, in order to prepare 2-(4'-bromophenyl-4-yl)pyridine, 3.92 g of 2-bromo pyridine (0.025 mol), 150 ml of tetrahydrofuran and a 2M potassium carbonate aqueous solution (20 ml) were added in a 250 ml double-necked, round-bottom flask under nitrogen atmosphere, and then palladium tetrakistriphenylphosphine (Pd(PPh$_3$)$_4$; 0.37 g, 3 mol %) as a catalyst was added. Then, 4-bromo phenyl boronic acid was slowly added dropwise thereto.

Figure 5:
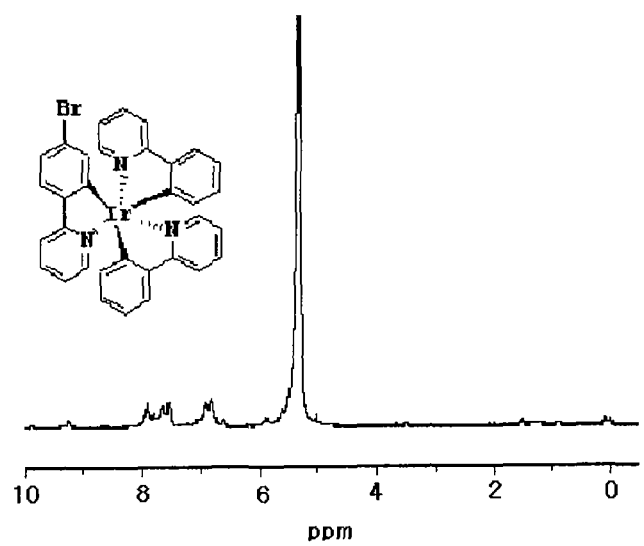
FIG. 5 illustrates the $^1$H-NMR spectrum of iridium(2-(4'-bromophenyl-4-yl) pyridine) (2-(2-(phenylpyridine))$_2$ prepared in Preparative Example 2 according to the present invention.

The mixture was refluxed at 80° C. for 24 hours, and separated in the same manner as in Preparative Example 2. The yield was 80%. Further, an $^1$H-NMR of the prepared 4-bromo phenyl pyridine is illustrated in the accompanying FIG. 5.

Then, 3.25 g of 4-bromo phenyl pyridine (0.014 mol), 3 g of iridium diphenyl pyridine complex (0.0028 mol), 1.43 g of silver-tri-fluoro-methane-sulfonate (0.0056 mol), 80 ml of 2-ethoxy ethanol were added in a 250 ml double-necked, round-bottom flask under nitrogen atmosphere. The mixture was refluxed at 130° C. for 24 hours, and the reaction was terminated. After reaction, in order to remove the residual silver chloride, the resultant was filtered with a glass filter, and 2-ethoxy ethanol was removed by distillation under reduced pressure. The resultant was washed with dimethyl chloride several times, and purified by column chromatography using dichloromethane as a developing solvent.

Figure 6:
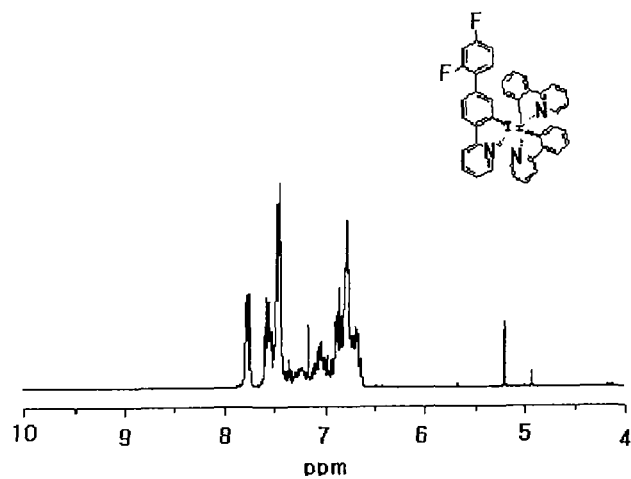
FIG. 6 illustrates the $^1$H-NMR spectrum of iridium(2-(4'-difluorophenyl-4-yl)pyridine)(2-(2-(phenylpyridine))$_2$ prepared in Preparative Example 3 according to the present invention.

Finally, by precipitation with 150 ml of tetrahydrofuran, iridium(2-(4'-bromophenyl-4-yl)pyridine)(2-(2-(phenylpyridine))$_2$ as in Reaction Scheme 2 can be obtained in a yield of 70%. The yield was 50%. An $^1$H-NMR of the prepared iridium(2-(4'-bromophenyl-4-yl)pyridine)(2-(2-(phenylpyridine))$_2$ is illustrated in the accompanying FIG. 6.

Preparative Example 4

Preparation of poly(3,6-diphenyl-9-decyl-carbazole)-random-poly(iridium(2-(4'-diphenyl-4-yl)pyridine) (2-(2-(phenylpyridine))$_2$) by Condensation Polymerization (CP0)

0.4 g of 3,6-dihydroxyphenyl-9-decyl-carbazole (0.0008 mol), 0.138 g of potassium carbonate, and 25 ml of toluene, and 10 ml of 1-methyl 2-pyrrolidinone were added to a 100 ml double-necked, round-bottom flask under nitrogen atmosphere, and refluxed at 160° C. for 10 hours. Then, 1.5 g of 2,4-difluoro phenyl pyridine (0.0008 mol) was added thereto.

Figure 7:
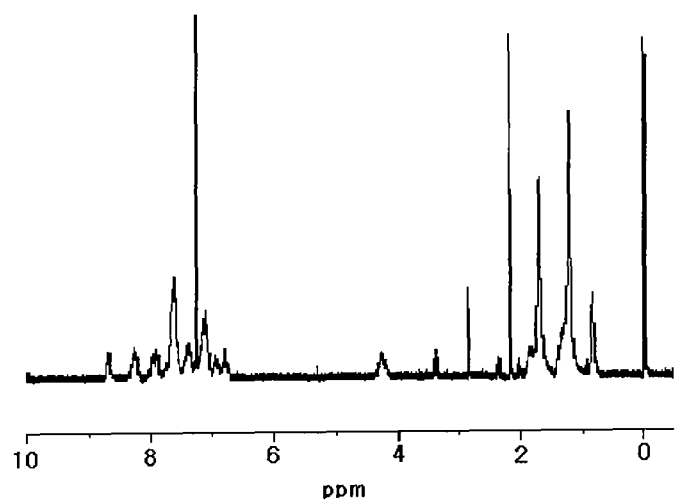
FIG. 7 illustrates the $^1$H-NMR spectrum of a copolymer, poly(3,6-diphenyl-9-decyl-carbazole)-random-poly(iridium (2-(4'-diphenyl-4-yl)pyridine)(2-(2-(phenylpyridine))$_2$) prepared in Preparative Example 4 according to the present invention.

The mixture was refluxed at 200° C. for 20 hours, and the reaction was terminated. The reaction mixture was slowly precipitated in 500 ml of methanol, and then filtered to remove methanol. The resultant was dried in a vacuum oven, and the yield was 80%. Further, an $^1$H-NMR of the prepared CP0 is illustrated in the accompanying FIG. 7.

Preparative Example 5

Preparation of poly(3,6-diphenyl-9-decyl-carbazole)-random-poly(iridium(2-(4'-diphenyl-4-yl)pyridine) (2-(2-(phenylpyridine))$_2$) by Condensation Polymerization (CP1)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.15 g of 2,4-difluoro phenyl pyridine (0.00079 mol), and 0.006 g of difluoro iridium complex (0.000008 mol) were added thereto.

The mixture was refluxed at 200° C. for 20 hours, and then the reaction was terminated. The reaction mixture was slowly precipitated in 500 ml of methanol, and then filtered to remove methanol. The resultant was dried in a vacuum oven, and the yield was 80%.

Preparative Example 6

Preparation of poly(3,6-diphenyl-9-decyl-carbazole)-random-poly(iridium(2-(4'-diphenyl-4-yl)pyridine) (2-(2-(phenylpyridine))$_2$) by Condensation Polymerization (CP3)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.148 g of 2,4-difluoro phenyl pyridine (0.000776 mol), and 0.018 g of difluoro iridium complex (0.000024 mol) were added thereto.

The mixture was refluxed at 200° C. for 20 hours, and then the reaction was terminated. The reaction mixture was slowly precipitated in 500 ml of methanol, and then filtered to remove methanol. The resultant was dried in a vacuum oven, and the yield was 80%.

Preparative Example 7

Preparation of poly(3,6-diphenyl -9-decyl-carbazole)-random-poly(iridium(2-(4'-diphenyl -4-yl)pyridine) (2-(2-(phenylpyridine))$_2$) by Condensation Polymerization (CP7)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.142 g of 2,4-difluoro phenyl pyridine (0.00074 mol), and 0.043 g of difluoro iridium complex (0.000056 mol) were added thereto.

The mixture was refluxed at 200° C. for 20 hours, and then the reaction was terminated. The reaction mixture was slowly precipitated in 500 ml of methanol, and then filtered to remove methanol. The resultant was dried in a vacuum oven, and the yield was 80%.

Preparative Example 8

Preparation of poly(3,6-diphenyl -9-decyl-carbazole)-random-poly(iridium(2-(4'-diphenyl -4-yl)pyridine) (2-(2-(phenylpyridine))$_2$) by Condensation Polymerization (CP12)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.134 g of 2,4-difluoro phenyl pyridine (0.0007 mol), and 0.073 g of difluoro iridium complex (0.000096 mol) were added thereto. The mixture was refluxed at 200° C. for 20 hours, and then the reaction was terminated. The reaction mixture was slowly precipitated in 500 ml of methanol, and then filtered to remove methanol. The resultant was dried in a vacuum oven, and the yield was 80%.

Preparative Example 9

Preparation of poly(3,6-diphenyl -9-decyl-carbazole)-random-poly(iridium(2-(4'-diphenyl -4-yl)pyridine) (2-(2-(phenylpyridine))$_2$) by Condensation Polymerization (CP40)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.091 g of 2,4-difluoro phenyl pyridine (0.00048 mol), and 0.245 g of difluoro iridium complex (0.00032 mol) were added thereto.

The mixture was refluxed at 200° C. for 20 hours, and then the reaction was terminated. The reaction mixture was slowly precipitated in 500 ml of methanol, and then filtered to remove methanol. The resultant was dried in a vacuum oven, and the yield was 80%.

The amount of sample added in order to prepare each compound described in Preparative Examples, yield or the like are summarized in the following Table 1.

TABLE 1

|  | DDHPCz[g] | DFPPy[g] | DFP-Ir[g] | Yield[%] | M.W | pd | Td[° C.] | Tg[° C.] |
|---|---|---|---|---|---|---|---|---|
| CP0 | 0.4 | 0.115 | 0 | 70 | 2135 | 1.08 |  |  |
| CP1 | 0.4 | 0.15 | 0.006 (1 mol %) | 73 | 3000 | 1.4 | 418 | 125 |
| CP3 | 0.4 | 0.148 | 0.018 (3 mol %) | 60 | 2700 | 1.5 | 404 | 120 |
| CP7 | 0.4 | 0.142 | 0.043 (7 mol %) | 77 | 2039 | 1.5 | 363 | 125 |
| CP12 | 0.4 | 0.134 | 0.073 (12 mol %) | 75 | 1662 | 1.3 | 357 | 125 |
| CP40 | 0.4 | 0.091 | 0.245 (40 mol %) | 78 | 1928 | 1.2 |  |  |

In Table 1, DDHPCz represents 3,6-dihydroxyphenyl-9-decyl-carbazole, DFPPy represents 2,4-difluoro phenyl pyridine, and DFP-Ir represents a difluoro iridium complex. M.W represents molecular weight, pd represents a polydispersion index, Td represents a decomposition temperature, and Tg represents a glass transition temperature.

Preparative Example 10

Preparation of poly(3,6-diphenyl -9-decyl-carbazole)-random-poly(iridium(3-(5'-diphenyl -4-yl)pyridine) (2-(2-(phenylpyridine))$_2$) by Condensation Polymerization (DP3)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.148 g of 2,4-difluoro phenyl pyridine (0.000776 mol), and 0.018 g of difluoro iridium complex (0.000024 mol) were added thereto.

Figure 8:
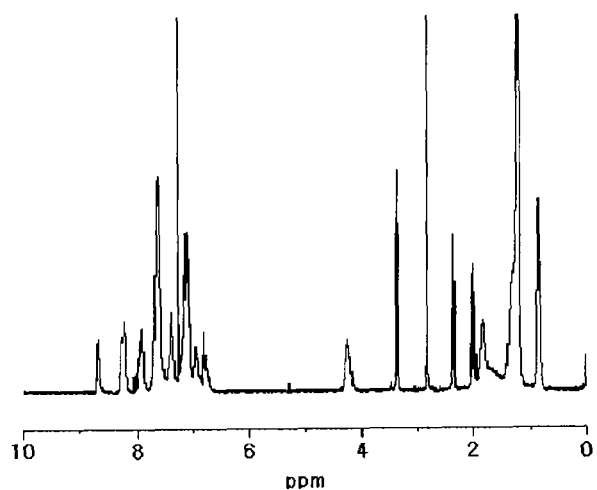
FIG. 8 illustrates the $^1$H-NMR spectrum of a copolymer, poly(3,6-diphenyl-9-decyl-carbazole)-random-poly(iridium (3-(5'-diphenyl-4-yl)pyridine)(2-(2-(phenylpyridine))$_2$) prepared in Example 10 according to the present invention.
Figure 9:
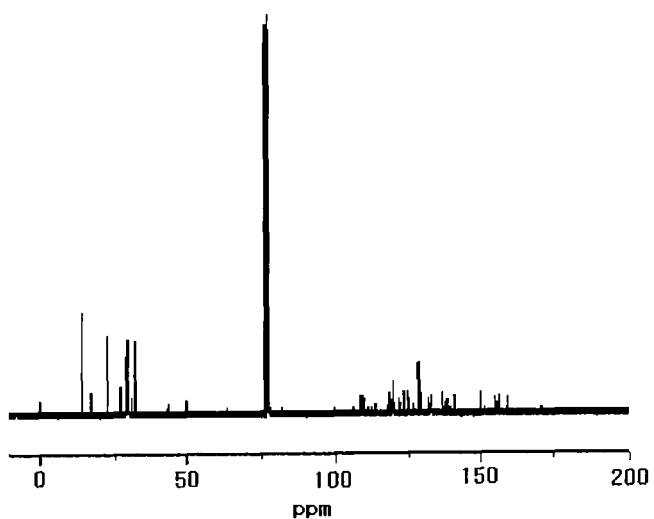
FIG. 9 illustrates the $^{13}$C-NMR spectrum of a copolymer, poly(3,6-diphenyl-9-decyl-carbazole)-random-poly(iridium (2-(4'-diphenyl-4-yl)pyridine)(2-(2-(phenylpyridine))$_2$) prepared in Example 6 according to the present invention.
Figure 10:
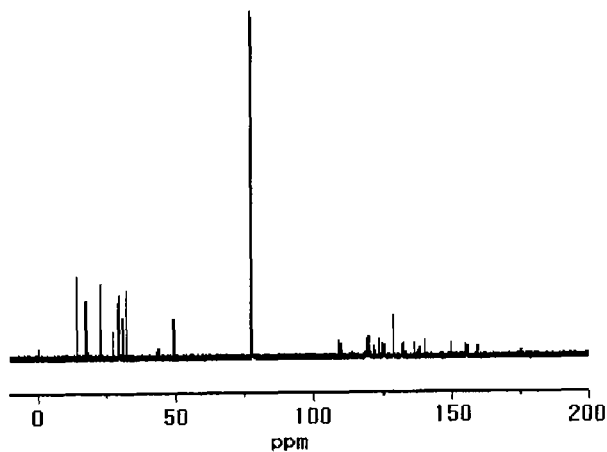
FIG. 10 illustrates the $^{13}$C-NMR spectrum of a copolymer, poly(3,6-diphenyl-9-decyl-carbazole)-random-poly(iridium (3-(5'-diphenyl-4-yl)pyridine)(2-(2-(phenylpyridine))$_2$) prepared in Example 10 according to the present invention.
Figure 11:
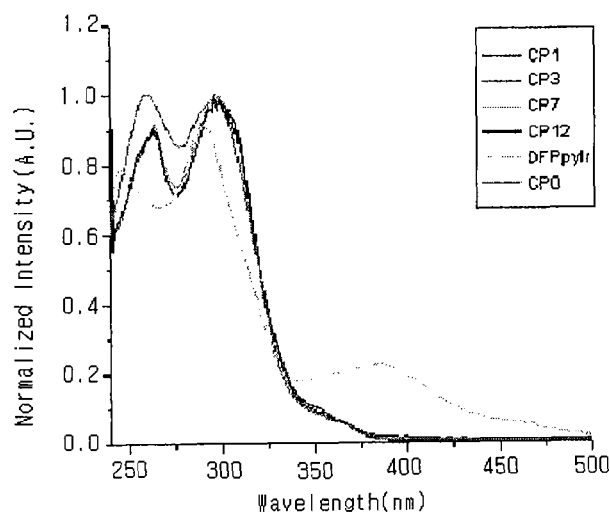
FIG. 11 illustrates the UV-vis spectrum of a copolymer, poly(3,6-diphenyl-9-decyl-carbazole)-random-poly(iridium (3-(5'-diphenyl-4-yl)pyridine)(2-(2-(phenylpyridine))$_2$) prepared in Examples 4 to 9 according to the present invention.
Figure 12:
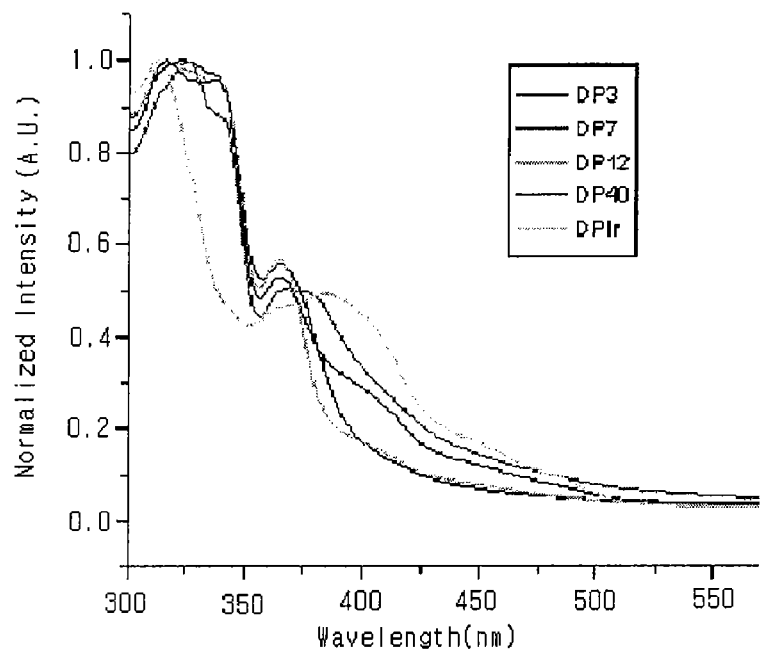
FIG. 12 illustrates the UV-vis spectrum of a copolymer, poly(3,6-diphenyl-9-decyl-carbazole)-random-poly(iridium (3-(5'-diphenyl-4-yl)pyridine)(2-(2-(phenylpyridine))$_2$) prepared in Examples 10 to 13 according to the present invention.
Figure 13:
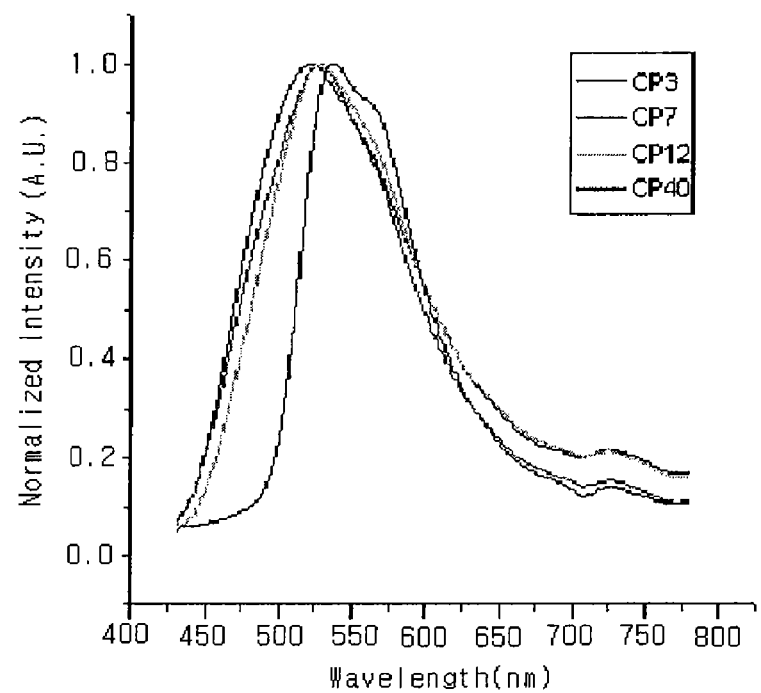
FIG. 13 illustrates the photoluminescence spectrum of a copolymer, poly(3,6-diphenyl-9-decyl-carbazole)-random-poly(iridium(2-(4'-diphenyl-4-yl)pyridine)(2-(2-(phenylpyridine))$_2$) prepared in Examples 4 to 9 according to the present invention.
Figure 14:
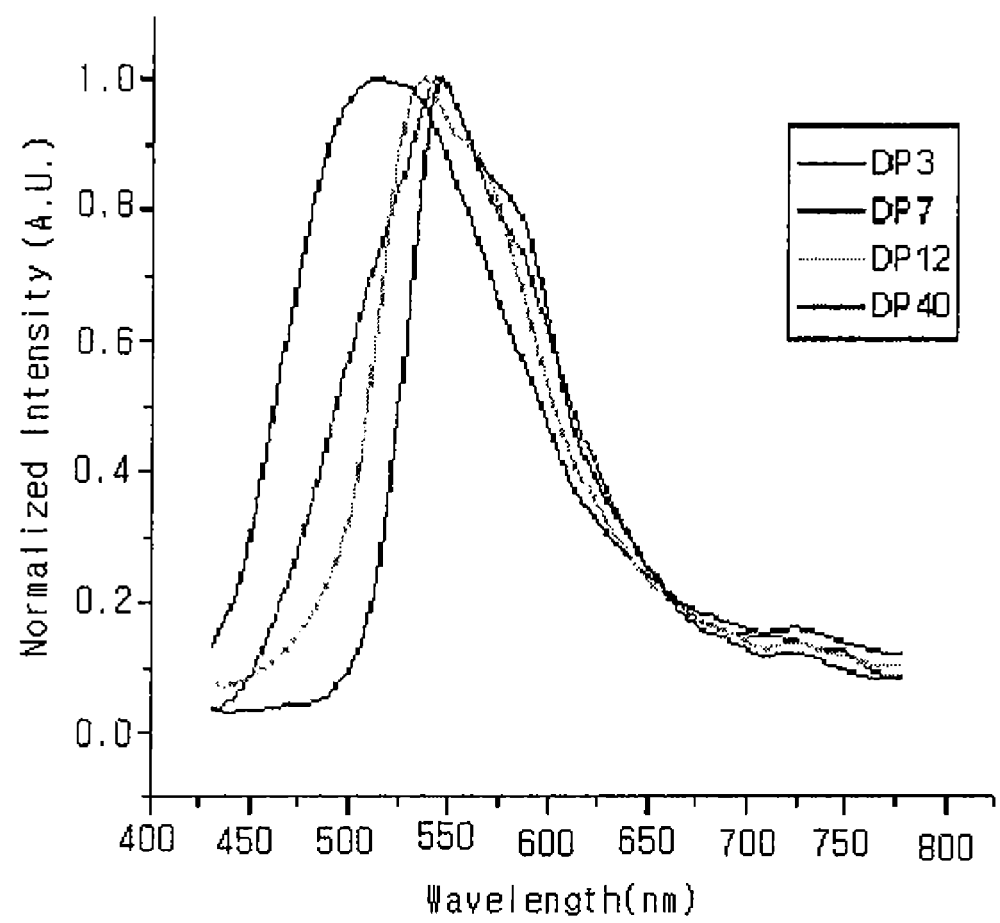
FIG. 14 illustrates the photoluminescence spectrum of a copolymer, poly(3,6-diphenyl-9-decyl-carbazole)-random-poly(iridium(3-(5'-diphenyl-4-yl)pyridine)(2-(2-(phenylpyridine))$_2$) prepared in Examples 10 to 13 according to the present invention.

The mixture was refluxed at 200° C. for 20 hours, and then the reaction was terminated. The reaction mixture was slowly precipitated in 500 ml of methanol, and then filtered to remove methanol. The resultant was dried in a vacuum oven, and the yield was 80%. Further, an $^1$H-NMR of the prepared DP3 is illustrated in the accompanying FIG. 8.

Preparative Example 11

Preparation of poly(3,6-diphenyl-9-decyl-carbazole)-random-poly(iridium(3-(5'-diphenyl -4-yl)pyridine) (2-(2-(phenylpyridine))$_2$) by Condensation Polymerization (DP7)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.142 g of 2,4-difluoro phenyl pyridine (0.000744 mol), and 0.043 g of difluoro iridium complex (0.000056 mol) were added thereto.

The mixture was refluxed at 200° C. for 20 hours, and then the reaction was terminated. The reaction mixture was slowly precipitated in 500 ml of methanol, and then filtered to remove methanol. The resultant was dried in a vacuum oven, and the yield was 80%.

Preparative Example 12

Preparation of poly(3,6-diphenyl-9-decyl-carbazole)-random-poly(iridium(3-(5'-diphenyl-4-yl)pyridine) (2-(2-(phenylpyridine))₂) by Condensation Polymerization (DP12)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.134 g of 2,4-difluoro phenyl pyridine (0.000704 mol), and 0.0736 g of difluoro iridium complex (0.000096 mol) were added thereto. The mixture was refluxed at 200° C. for 20 hours, and then the reaction was terminated. The reaction mixture was slowly precipitated in 500 ml of methanol, and then filtered to remove methanol. The resultant was dried in a vacuum oven, and the yield was 80%.

Preparative Example 13

Preparation of poly(3,6-diphenyl-9-decyl-carbazole)-random-poly(iridium(3-(5'-diphenyl -4-yl)pyridine) (2-(2-(phenylpyridine))₂) by Condensation Polymerization (DP40)

Under the same conditions as in Preparative Example 4, 0.4 g of 3,6-dihydroxyphenyl-9-decyl-carbazole (0.0008 mol), 0.138 g of potassium carbonate, 25 ml of toluene, and 10 ml of 1-methyl 2-pyrrolidinone were added, and refluxed at 160° C. for 10 hours. Then, 0.091 g of 2,4-difluoro phenyl pyridine (0.00048 mol), and 0.245 g of difluoro iridium complex (0.00032 mol) were added thereto. The mixture was refluxed at 200° C. for 20 hours, and then the reaction was terminated.

The reaction mixture was slowly precipitated in 500 ml of methanol, and then filtered to remove methanol. The resultant was dried in a vacuum oven, and the yield was 80%.

The amount of sample added in order to prepare each compound described in Preparative Examples, yield or the like are summarized in the following Table 2.

In Table 2, DHP-Cz represents 3,6-dihydroxyphenyl-9-decyl-carbazole, and other abbreviated words are the same as described in Table 1.

According to the above described method, in the present invention, a monomer of carbazole derivative having an excellent hole transporting capability is synthesized, and an iridium complex, which is one of transition metals efficiently forming phosphorescence by spin-orbital coupling in an organic light emitting device, is synthesized as a monomer. Further, a copolymer comprising the monomers in its main chain is synthesized by condensation polymerization of the monomers. The carbazole derivative and iridium complex are contained in the main chain of the prepared copolymer, whereby energy transfer efficiently occurs, and a stable and efficient organic light emitting device can be manufactured.

According to the present invention as described above, the carbazole derivative and iridium complex form the main chain of copolymer. Therefore, energy transfer can easily occur through the main chain, thereby having higher luminous efficiency. Further, since monomers are contained in the main chain, the copolymer has a high glass transition temperature to be chemically stable. Further, phase separation or ionic aggregation is prevented, thereby capable of preparing an efficient and stable light emitting material by using the copolymer according to the present invention as a polymer light emitting material.

Although the present invention has been described in connection with the preferred Examples of the present invention, it will be apparent to those skilled in the art that various modifications and changes may be made thereto without departing from the scope and spirit of the present invention described in the appended claims.

What is claimed is:

1. A random copolymer having an iridium complex and carbazole derivative, represented by the following Formula 4:

[Formula 4]

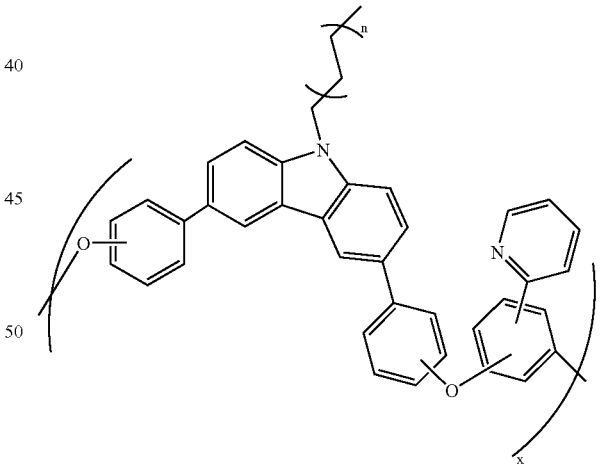

TABLE 2

|      | DHP-Cz[g] | DFPPy[g] | mol % | DF-Ir[g] | Yeild[%] | M.W  | pd  | Tg/Td[° C.] |
|------|-----------|----------|-------|----------|----------|------|-----|-------------|
| DP3  | 0.4       | 0.142    | 3     | 0.018    | 75       | 3902 | 1.6 |             |
| DP7  | 0.4       | 0.142    | 7     | 0.043    | 76       | 2200 | 1.6 |             |
| DP12 | 0.4       | 0.134    | 12    | 0.073    | 80       | 2020 | 2.2 |             |
| DP40 | 0.4       | 0.091    | 40    | 0.245    | 66       | 2021 | 2.1 |             |

-continued

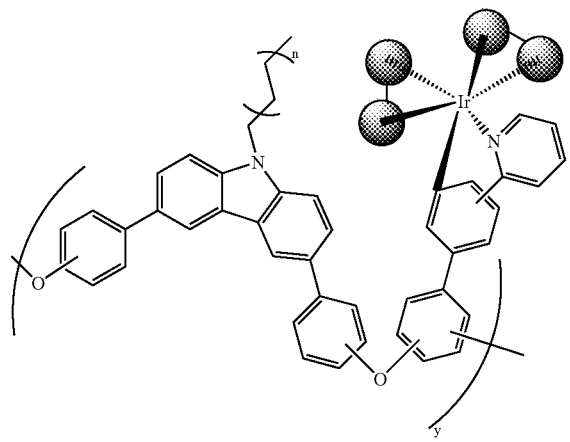

wherein a molecular weight of the random co-polymer is 1000 to 900000, x+y is 100, and n is 1 to 10, respectively, and wherein the ligand is selected from the group consisting of structures described in the following Table

| Ligand | |
|---|---|
| Name | Structure |
| 2-Phenyl-pyridine | |
| 2-p-Tolyl-pyridine | 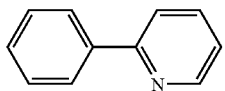 |
| 2-(4-Fluoro-phenyl)-pyridine | 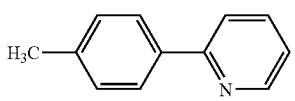 |
| 2-(2,4-Difluoro-phenyl)-pyridine | 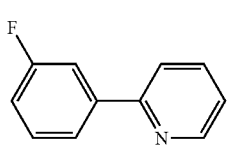 |
| Benzo[α]quinoline | 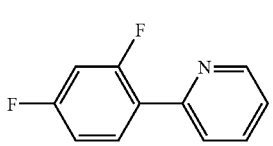 |

-continued

| Ligand | |
|---|---|
| Name | Structure |
| 1-Phenylisoquinoline | 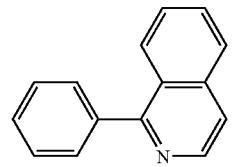 |
| 1-Naphthalen-2-yl-isoquinoline | 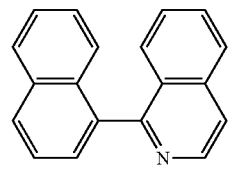 |
| 2-Thiophen-2-yl-pyridine | 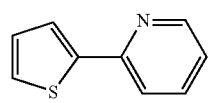 |
| 2-Phenyl-benzothiozole | 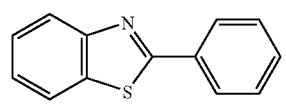 |
| 2-Phenyl-benzoenzooxezole | 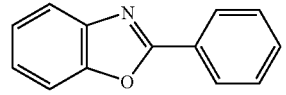 |
| 4-(5-ethylthio)-1H-tetrazol-1-yl)-2-fluorobenzonitrile | 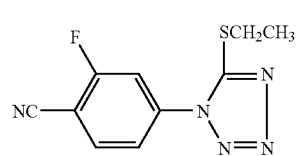 |
| 2-Biphenyl-4-yl-pyridine | 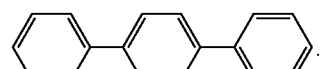 |

2. A method for preparing a random copolymer having an iridium complex and carbazole derivative by the following Reaction Scheme 1:

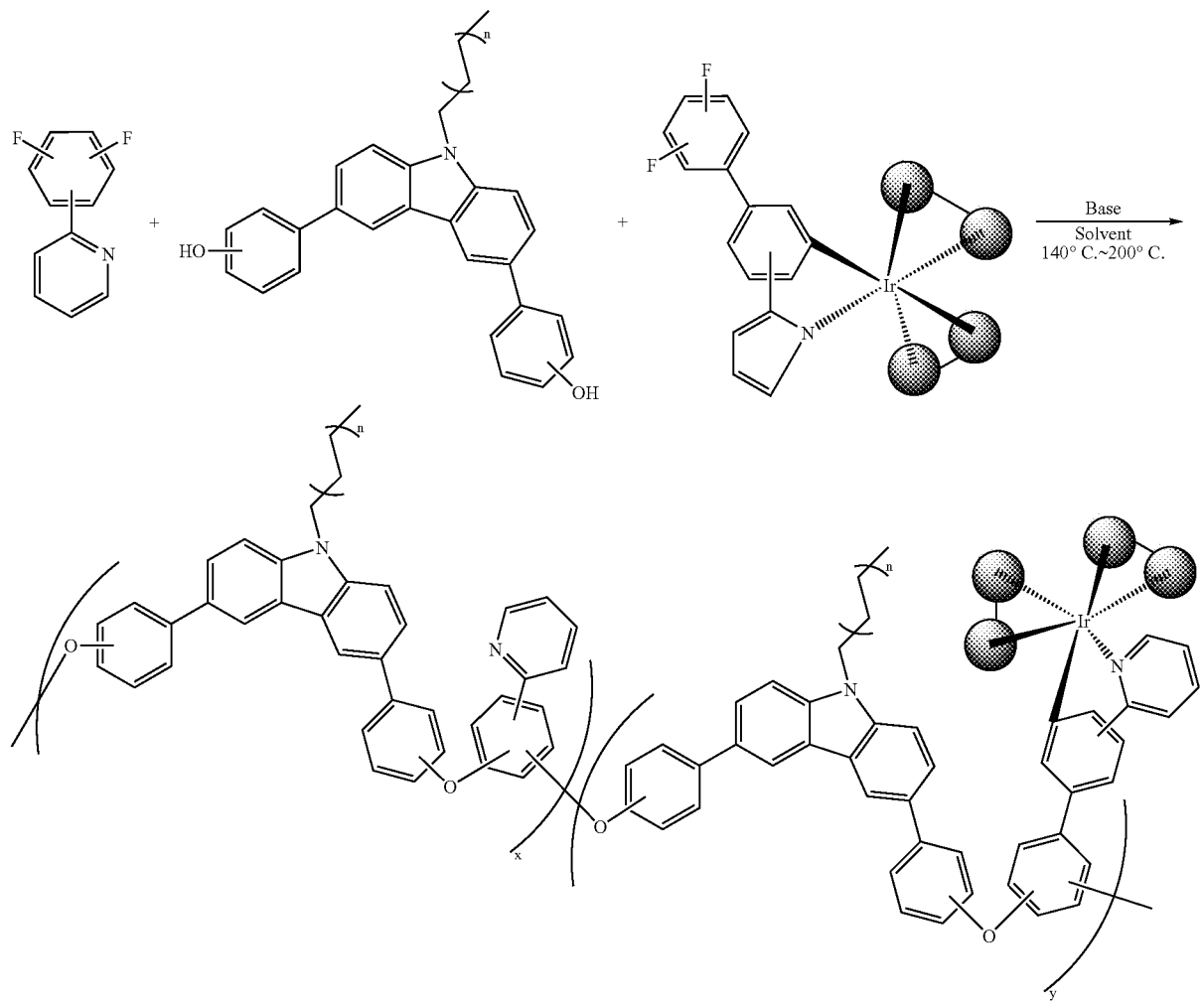
wherein a molecular weight of the random copolymer is 1000 to 900000, x+y is 100, and n is 1 to 10, respectively, and
wherein the ligand is selected from the group consisting of structures described in the following Table
| | Ligand |
|---|---|
| Name | Structure |
| 2-Phenyl-pyridine | |
| 2-p-Tolyl-pyridine | |
-continued
| | Ligand |
|---|---|
| Name | Structure |
| 2-(4-Fluoro-phenyl)-pyridine | |
| 2-(2,4-Difluoro-phenyl)-pyridine | |
| Benzo[α]quinoline | |

-continued

| Ligand | |
|---|---|
| Name | Structure |
| 1-Phenylisoquinoline | 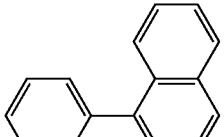 |
| 1-Naphthalen-2-yl-isoquinoline | 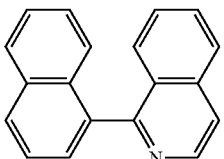 |
| 2-Thiophen-2-yl-pyridine | 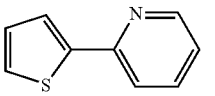 |
| 2-Phenyl-benzothiozole | 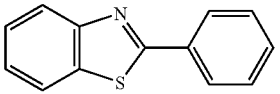 |
| 2-Phenyl-benzoenzooxezole | 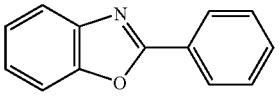 |

-continued

| Ligand | |
|---|---|
| Name | Structure |
| 4-(5-ethylthio)-1H-tetrazol-1-yl)-2-fluorobenzonitrile | 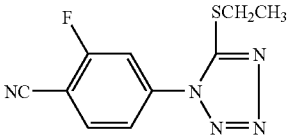 |
| 2-Biphenyl-4-yl-pyridine | 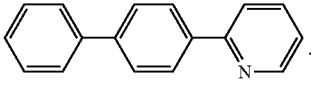 |

3. The method according to claim 2, wherein the monomer with a difluoro group is synthesized by reacting bromopyridine with difluoro phenyl boronic acid by Suzuki coupling reaction.

4. The method according to claim 2, wherein in Reaction Scheme I, the polymer is synthesized by activating the dihydroxy phenyl carbazole derivative, and by adding the monomer with a difluoro group and the difluoro-phenyliridium complex.

5. The method according to claim 4, wherein as a reaction solvent to activate the dihydroxy phenyl carbazole derivative, 1-methyl pyrrolidone, dimethyl-form-amide or dimethyl-sulfoxide is used.

6. The method according to claim 4, wherein the dihydroxy phenyl carbazole derivative is activated in the presence of an alkali metal base.

* * * * *